(12) United States Patent
Kim

(10) Patent No.: US 9,778,017 B2
(45) Date of Patent: Oct. 3, 2017

(54) APPARATUS FOR MEASURING THICKNESS OF POWDER DEPOSITED ON INNER SURFACE OF PIPE

(71) Applicant: Kwang-Youn Kim, Gyeonggi-do (KR)

(72) Inventor: Kwang-Youn Kim, Gyeonggi-do (KR)

(73) Assignee: Kwang-Youn Kim, Gyeonggi-do (KR)

( * ) Notice: Subject to any disclaimer, the term of this patent is extended or adjusted under 35 U.S.C. 154(b) by 0 days.

(21) Appl. No.: 14/557,367

(22) Filed: Dec. 1, 2014

(65) Prior Publication Data
US 2017/0176165 A1    Jun. 22, 2017

(51) Int. Cl.
G01R 27/22  (2006.01)
G01R 27/26  (2006.01)
G01B 7/06   (2006.01)
G01N 27/22  (2006.01)
G01N 33/00  (2006.01)

(52) U.S. Cl.
CPC ........... *G01B 7/085* (2013.01); *G01N 27/221* (2013.01); *G01N 33/00* (2013.01); *G01N 2033/0091* (2013.01)

(58) Field of Classification Search
CPC .. G01R 27/2605; G01N 17/04; G01N 17/006; G01N 17/02; G01N 27/20; G01N 27/041; G01N 33/20; G01N 1/00; G01N 2201/00; G01N 22/00; G01N 27/04; G01N 27/048; G01N 27/125; G01N 27/221; G01N 27/226
USPC ....... 324/700, 347, 358, 370, 444, 447, 449, 324/515, 559, 229, 635, 644, 699, 716, 324/658–690
See application file for complete search history.

(56) References Cited

U.S. PATENT DOCUMENTS

| | | | | |
|---|---|---|---|---|
| 3,231,815 A | * | 1/1966 | Spencer | G01N 15/1031 324/675 |
| 3,390,325 A | * | 6/1968 | Shawhan | G01R 27/26 324/123 R |
| 5,151,660 A | * | 9/1992 | Powers | G01L 9/0005 324/663 |
| 5,214,386 A | * | 5/1993 | Singer | G01N 15/0266 324/452 |
| 6,388,452 B1 | * | 5/2002 | Picciotto | B41J 11/0035 324/452 |
| 6,496,258 B1 | * | 12/2002 | Leipertz | G01N 15/0205 356/336 |

(Continued)

FOREIGN PATENT DOCUMENTS

KR    101221619 B1 *  1/2013    ............... G01B 7/06

*Primary Examiner* — Patrick Assouad
*Assistant Examiner* — Taqi Nasir
(74) *Attorney, Agent, or Firm* — The PL Law Group, PLLC

(57) ABSTRACT

Provided is an apparatus capable of distinguishing a kind of a powder deposited on an inner surface of a pipe, and more precisely measuring a thickness of the powder deposited on the inner surface of the pipe. The apparatus for measuring a thickness of a powder deposited on an inner surface of a pipe, includes a pair of the first electrodes disposed adjacent to one portion of the inner surface of the pipe and used to measure a first capacitance and thus to distinguish a kind of the powder, and a pair of second electrodes disposed in the pipe to be spaced from each other and to be symmetrical with respect to a center portion of the pipe and used to measure a second and a third capacitance.

18 Claims, 3 Drawing Sheets

(56) References Cited

U.S. PATENT DOCUMENTS

| | | | |
|---|---|---|---|
| 7,518,380 B2* | 4/2009 | Bonne | G01F 1/6845 |
| | | | 324/663 |
| 2005/0093555 A1* | 5/2005 | Ehata | H01P 7/06 |
| | | | 324/672 |
| 2011/0284380 A1* | 11/2011 | Martin | B82B 3/00 |
| | | | 204/622 |

* cited by examiner

APPARATUS FOR MEASURING THICKNESS OF POWDER DEPOSITED ON INNER SURFACE OF PIPE

CROSS-REFERENCE TO RELATED APPLICATION

This application claims priority to and the benefit of Korean Patent Application No. 2014-0087318, filed on Jul. 14, 2014, the disclosure of which is incorporated herein by reference in its entirety.

BACKGROUND

1. Field of the Invention

The present invention relates to an apparatus for measuring a thickness of a powder deposited on an inner surface of a pipe, and more particularly, to an apparatus which is capable of more precisely measuring a thickness of a dielectric powder deposited on an inner surface of a pipe by identifying a kind of the dielectric powder deposited in the pipe.

2. Discussion of Related Art

In a pipe or the like connected to a vacuum chamber for producing a semiconductor, an LCD, an LED, an MEMS or the like, the inside of which should be evacuated, or from which gas should be continuously discharged, the gas includes fine powder, and the powder is deposited on an inner surface of the pipe during the continuous discharge operation. The deposited powder decreases a diameter of the pipe, which in turn causes the discharge operation to take a longer period of time, and/or a backflow phenomenon. Such backflow phenomenon may result in, for example, a damage of a wafer or a fire outbreak.

There has been an effort to inhibit such a problem, periodically replacing a pipe and applying heat from an outside to a pipe so as to delay a deposition cycle. On the other hand, an apparatus for measuring a thickness of a powder deposited on an inner surface of a pipe has been developed.

An example of such apparatus has been disclosed in Korean Patent No. 10-1221619. The conventional apparatus described herein includes one or more electrode parts having an electric charge surface corresponding to a partial shape of an inner circumstantial surface of a pipe, and a capacitance measuring part conductively connected with the electrode parts and configured to measure a capacitance. A method of measuring a thickness of a powder deposited on an inner surface of a pipe with the conventional apparatus configured as above-mentioned is as follows. That is, first the conventional apparatus is installed at a clean pipe in which the powder is not deposited, and the capacitance is measured. This capacitance is set as a reference value. Then, the pipes in which a powder has been deposited on the inner surface thereof are collected, and thicknesses of the powder are measured. After that, the conventional apparatus is installed at each of the collected pipes to measure capacitances, and thus obtained capacitances are set as comparison values. Next, the reference value and the comparison values are stored in a database, and the conventional apparatus is installed at a pipe to be inspected, and measures a capacitance to obtain a thickness of the powder deposited in the inner surface of the pipe.

However, if the conventional apparatus is installed in a pipe in which a different kind of powder from the powder corresponding to the reference value and comparison values stored in the database is deposited, the conventional apparatus may provide inaccurate information regarding a thickness of the powder deposited on the inner surface of the pipe. In other words, since a different kind of a powder has a different relative dielectric constant, if the reference value and the comparison values obtained from a different kind of powder are used to obtain the thickness of a powder deposited on an inner surface of a pipe, the conventional apparatus may provide inaccurate thickness information.

SUMMARY

The present invention is directed to an apparatus capable of identifying a kind of a powder deposited on an inner surface of a pipe and more accurately measuring a thickness of the powder deposited on the inner surface of the pipe.

According to an aspect of the present invention, there is provided an apparatus for measuring a thickness of a powder deposited on an inner surface of a pipe, which includes a capacitance measurement part for measuring a capacitance, the apparatus comprising:

a pair of first electrodes spaced from each other, and disposed adjacent to one portion of the inner surface of the pipe; and a pair of second electrodes spaced from each other symmetrically relative to a center portion of the pipe, and attached to the inner surface of the pipe, wherein the pair of the first electrodes and the pair of the second electrodes are connected to the capacitance measurement part, wherein a relative dielectric constant of the powder ($\epsilon_r/\epsilon_0$) is calculated using the following Equation:

$$\epsilon_r/\epsilon_0 = C \cdot d/A \qquad \text{Equation}$$

where $\epsilon_r$ is a dielectric constant of the powder, $\epsilon_0$ is a dielectric constant of vacuum, C is a first capacitance corresponding to a capacitance measured between the pair of the first electrodes when it is not changed, d is a gap between the pair of the first electrodes, and A is a surface area of the first electrode, and wherein a kind of the powder may be identified by the calculated relative dielectric constant of the powder.

According to another aspect of the present invention, there is provided an apparatus for measuring a thickness of a powder deposited on an inner surface of a pipe, comprising:

a housing for being connected to the pipe;

a pair of first electrodes spaced from each other, and disposed adjacent to one portion of an inner surface of the housing;

a pair of second electrodes spaced from each other symmetrically relative to a center portion of the housing, and attached to the inner surface of the housing; and a capacitance measurement and relative dielectric constant calculation unit connected to the pair of the first electrodes and the pair of the second electrodes, wherein the capacitance measurement and relative dielectric constant calculation unit calculates a relative dielectric constant of the powder ($\epsilon_r/\epsilon_0$) by inputting a first capacitance corresponding to a capacitance measured between the pair of the first electrodes when it is not changed, into the following Equation:

$$\epsilon_r/\epsilon_0 = C \cdot d/A \qquad \text{Equation}$$

where $\epsilon_r$ is a dielectric constant of the powder, $\epsilon_0$ is a dielectric constant of vacuum, C is the first capacitance, d is a gap between the pair of the first electrodes, and A is a surface area of the first electrode.

According to yet another aspect of the present invention, there is provided a method of measuring a thickness of a powder deposited on an inner surface of a pipe, comprising:

measuring a first capacitance at a pair of first electrodes spaced from each other, and disposed adjacent to one portion of the inner surface of the pipe, the first capacitance corresponding to a capacitance measured between the pair of the first electrodes when it is not changed;

identifying a kind of powder deposited on the inner surface of the pipe from a relative dielectric constant ($\epsilon_r/\epsilon_0$) calculated by inputting the first capacitance into the following Equation (1);

$$\epsilon_r/\epsilon_0 = C \cdot d/A \qquad \text{Equation (1)}$$

where $\epsilon_r$ is a dielectric constant of the powder, $\epsilon_0$ is a dielectric constant of vacuum, C is the first capacitance, d is a gap between the pair of the first electrodes, and A is a surface area of the first electrode, measuring a second capacitance at a pair of second electrodes spaced from each other symmetrically relative to a center portion of the pipe, and attached to the inner surface of the pipe;

calculating a third capacitance of the pair of the second electrodes corresponding to a state at which the identified powder is full between the pair of the second electrodes, the third capacitance being calculated using the following Equation (2);

$$\epsilon_r/\epsilon_0 = C \cdot d/A \qquad \text{Equation (2)}$$

where $\epsilon_r/\epsilon_0$ is the relative dielectric constant of the powder, C is the third capacitance, d is a gap between the pair of the second electrodes, and A is a surface area of the second electrode, and comparing the second capacitance with the third capacitance.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. However, the embodiments are just preferable examples for the purpose of illustrations only not intended to limit the scope of the invention.

In the following description, detailed descriptions of well-known functions or constructions will be omitted when it is considered that such description would obscure the invention. Also, the terms used herein are defined according to the functions of the present invention. Thus, the terms may vary depending on user's or operator's intentions or practices. Therefore, the terms used herein must be understood based on the entire descriptions made herein.

The technical spirit of the invention is determined by claims, and the embodiments described herein serve just as a means of effectively explaining the present invention to a person skilled in the art.

Figure 1:
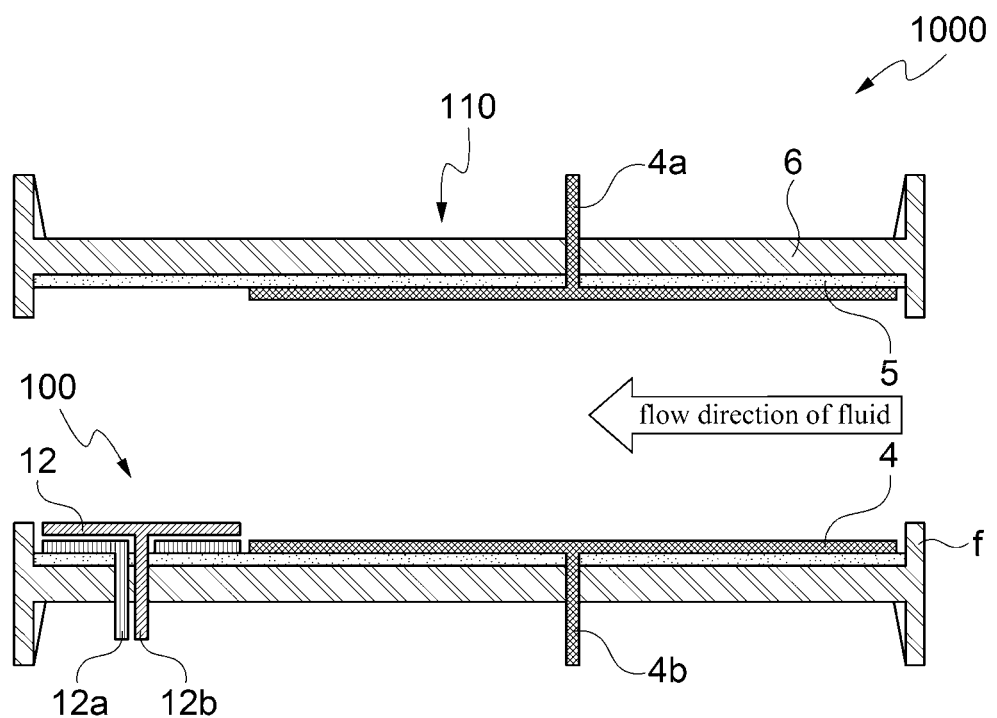
FIG. 1 is a schematic cross-sectional view of an apparatus for measuring a powder thickness according to a first embodiment of the present invention.

FIG. 1 is a schematic longitudinal cross-sectional view of an apparatus for measuring a thickness of powder deposited on an inner surface of a pipe according to a first embodiment of the present invention.

Referring to FIG. 1, the apparatus 1000 for measuring the powder thickness according to the first embodiment of the present invention includes a hollow housing 6, a first electrode part 100 installed at the hollow housing 6 and used to measure a relative dielectric constant, and a second electrode part 110 installed at the hollow housing 6 and used to measure a capacitance.

Figure 3A:
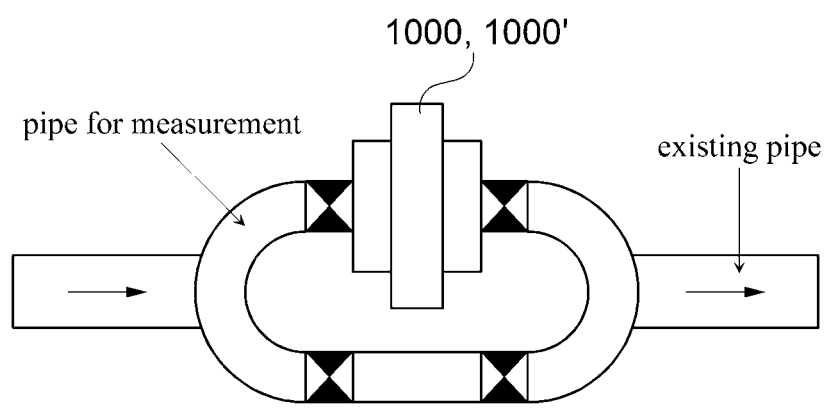
FIGS. 3A and 3B are views schematically illustrating a method of connecting a pipe of the apparatus for measuring the powder thickness to an existing pipe.
Figure 3B:
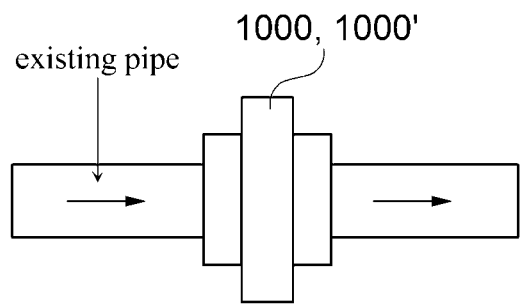

The hollow housing 6 is connected to a pipe in which a thickness of the deposited powder is to be measured. As illustrated in FIGS. 3A and 3B, the connection may be made by using a bypass pipe separately provided (FIG. 3A) or by being disposed in the middle of the existing pipe (FIG. 3B).

Further, if the hollow housing 6 is formed of a metallic material, an insulation layer 5 may be disposed on the inner surface of the hollow housing 6, as illustrated in FIG. 1. The cross section of the hollow housing 6 may be a circular shape and an inner diameter thereof may be, for example, 25, 40, 50, 100, 150 and 1000 mm. Further, the cross section of the hollow housing 6 may have a shape other than the circular shape, as long as the electrodes can be installed thereat. A flange part f for connection to the pipe to be inspected can be provided at both ends of the hollow housing 6. The flange part f may extend in an inside direction as well as in an outside direction of the hollow housing 6. One portion of the flange part f, which extends in the inside direction of the hollow housing 6, sticks out vertically from an inner surface of the hollow housing 6, but may be inclined in a reverse direction against a flow of a fluid flowing in the pipe.

Further, the hollow housing 6 may be omitted when a first and second electrode parts 100 and 110 are installed directly at the pipe in which the thickness of the deposited powder is to be measured. In this case, instead of the flange part f, a protrusion member can be used as described later.

The first electrode part 100 used to calculate the relative dielectric constant of the powder deposited in the housing 6 includes the pair of first electrodes 12 which is spaced from each other, disposed adjacent to one portion of the inner surface of the pipe and used to measure, and conductive members 12a and 12b conductively connected to the first electrodes 12. The conductive members 12a and 12b are connected to a capacitance measurement part (not shown), such as, for example, an RC oscillation circuit using a well-known OP Amp, to measure the capacitance. On the other hand, the first electrodes 12 may be separately used to measure static electricity. The measured static electricity may be used for determining whether it exerts an influence on a phenomenon in which the powder is deposited.

The second electrode part 110 used to measure the capacitance includes the pair of second electrodes 4 disposed in the hollow housing 6 so as to be opposite to each other or be symmetrical in a diameter direction with respect to a center portion of the hollow housing 6 and so as to be spaced a distance corresponding to about an inner diameter of the hollow housing 6, and the conductive members 4a and 4b conductively connected to the second electrodes 4, respectively, and configured to pass through a circumferential wall of the hollow housing 6. The conductive members 4a and 4b are connected to the capacitance measurement part for measuring the capacitance.

The first electrodes 12 of the first electrode part 100 may be located at a downstream side of the second electrodes 4 of the second electrode part 110 in a flow direction of the fluid flowing in the hollow housing 6. The first electrodes 12 are disposed to be adjacent to the flange part f. A gap between the first electrodes 12 is about a few millimeters. One of the first electrodes 12, which is further adjacent to the center portion of the hollow housing 6, may be located at a position having about the same height as that of an internally protruding portion of the flange part f The insulation layer 5 may be disposed between the hollow housing 6 and the other one of the first electrodes 12, which is adjacent to an inner surface of the hollow housing 6.

If the hollow housing 6 is connected to the pipe in another method other than that using the flange part f, or the hollow housing 6 is not used as described above, a protrusion member which is adjacent to the first electrodes 12 and has a similar structure to the internally protruding portion of the flange part f may be provided at a downstream side of the first electrodes 12 in the flow direction of the fluid flowing in the hollow housing 6 or the pipe.

According to the apparatus 1000 for measuring the powder thickness according to the first embodiment of the present invention, which is configured as described above, the relative dielectric constant of the powder can be obtained by using the capacitance measured at the first electrode part 100. That is, when the powder is deposited and full between the first electrodes 12, the capacitance (hereinafter, referred to as a "first capacitance") measured by the capacitance measurement part connected to the conductive members 12a and 12b of the first electrodes 12 is input into the following Equation, and thus the relative dielectric constant of the powder is calculated.

$$\epsilon_r = C \cdot d / A \cdot \epsilon_0 \quad \text{Equation}$$

Here, $\epsilon_r$ is a dielectric constant of the powder, $\epsilon_0$ is a dielectric constant of vacuum, C is the first capacitance, d is a gap (a predetermined certain value) between the first electrodes 12, and A is a surface area (a predetermined certain value) of the first electrode.

Since the relative dielectric constant is an intrinsic property of a material, a kind of the powder deposited between the first electrodes 12 can be identified by using the calculated relative dielectric constant. Then, a capacitance corresponding to the state at which the pipe is full of the powder (hereinafter, referred to as a "third capacitance") can be calculated. After that, a capacitance currently measured in real time between the second electrodes 4 (hereinafter, referred to as a "second capacitance") is compared with the third capacitance, and thus an amount of the powder deposited in the hollow housing 6 or the pipe can be obtained.

Figure 2:
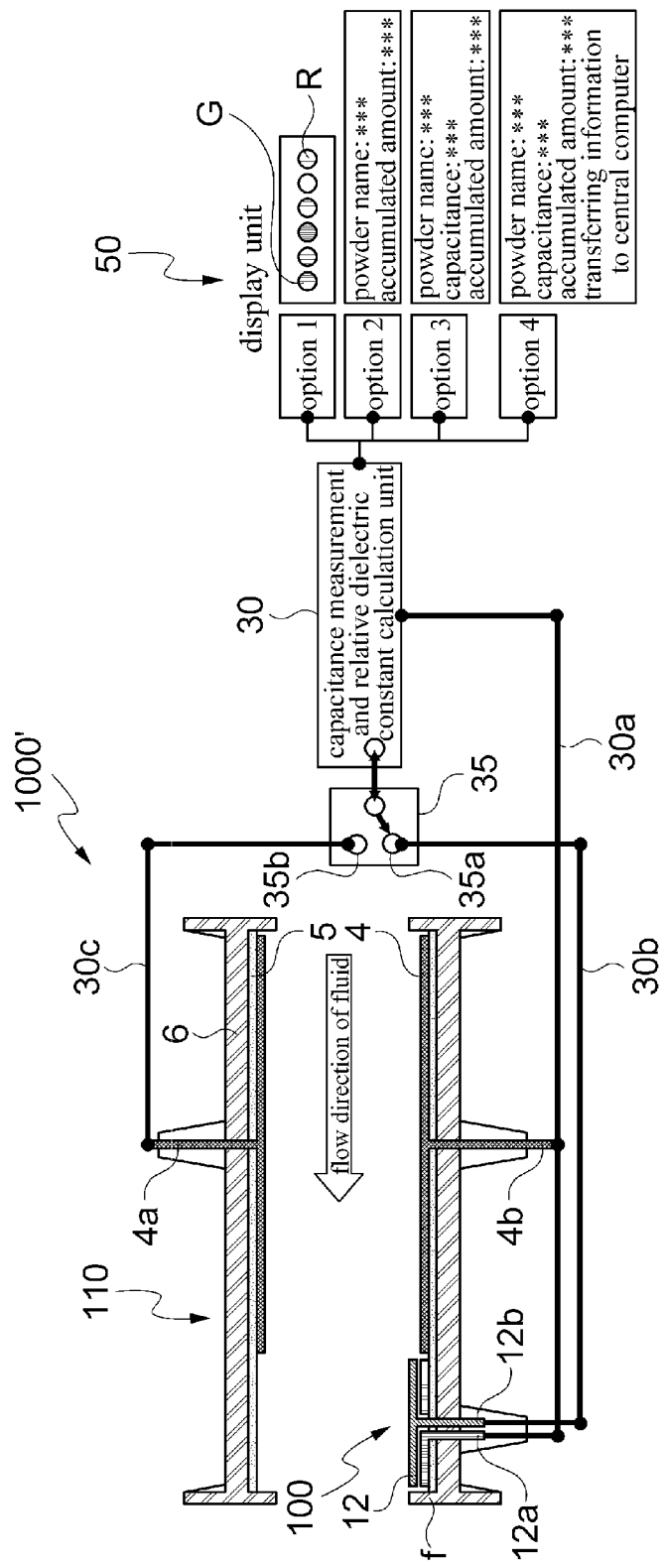
FIG. 2 is a schematic cross-sectional view of an apparatus for measuring a powder thickness according to a second embodiment of the present invention.

FIG. 2 is a schematic longitudinal cross-sectional view of an apparatus 1000' for measuring a thickness of powder deposited on an inner surface of a pipe according to a second embodiment of the present invention.

In describing the apparatus 1000' for measuring the powder thickness according to the second embodiment of the present invention, the same reference numerals are given to the same parts as those in the apparatus 1000 for measuring the powder thickness according to the first embodiment, and the description thereof will be omitted for simplicity.

As illustrated in FIG. 2, in contrast to the apparatus 1000 for measuring the powder thickness according to the first embodiment, the apparatus 1000' for measuring the powder thickness according to the second embodiment further includes a capacitance measurement and relative dielectric constant calculation unit 30, and a display unit 50 configured to display measured or obtained results. Further, a connection switching part 35 may be disposed between the conductive members 12a and 12b of the first electrodes 12, the conductive members 4a and 4b of the second electrodes 4 and the capacitance measurement and relative dielectric constant calculation unit 30.

The conductive member 4a is connected to a terminal 35b of the connection switching part 35 through a line 30c. The conductive members 12a and 4b are connected to the capacitance measurement and relative dielectric constant calculation unit 30 through the line 30a. The conductive member 12b is connected to a terminal 35a of the connection switching part 35 through a line 30b. The connection switching part 35 selectively connects the capacitance measurement and relative dielectric constant calculation unit 30 with the terminal 35a or the terminal 35b.

The lines 30a to 30c may be a LAN cable, or wireless Wi-Fi may be used for them.

The display unit 50 can display values calculated from the capacitance measurement and relative dielectric constant calculation unit 30 to operators with various options. As illustrated in FIG. 2, in an option 1, as the amount of the powder deposited in the hollow housing 6 is increased, the number of lighting parts is gradually increased from a green lighting part G toward a red lighting part R. An option 2 displays the kind of the powder which is currently being deposited, and an accumulated amounted of the powder deposited in the pipe. An option 3 further displays the capacitance in contrast to the option 2. In an option 4, information is displayed in the same way as in the option 3, and displayed information is transferred to a separate central computer (not shown).

According to the apparatus 1000' for measuring the powder thickness according to the second embodiment, which is configured as described above, first, when the powder is full between the first electrodes 12 (for example, at a state in which the capacitance measured between the first electrodes 12 is not changed), a signal indicative of the capacitance measured between the first electrodes 12 is transferred to the capacitance measurement and relative dielectric constant calculation unit 30 connected to the terminal 35a of the connection switching part 35. Then, the capacitance measurement and relative dielectric constant calculation unit 30 derives the first capacitance according to the signal from the first electrodes 12, for example, by using the RC oscillation circuit including the well-known OP Amp. Also, the capacitance measurement and relative dielectric constant calculation unit 30 calculates the relative dielectric constant by using the first capacitance and the above-mentioned equation.

Then, the capacitance measurement and relative dielectric constant calculation unit 30 can identify the kind of the powder deposited in the hollow housing 6 or the pipe by using the calculated relative dielectric constant. And the capacitance measurement and relative dielectric constant calculation unit 30 calculates the third capacitance of the pair of the second electrodes 4 corresponding to the state at which the identified powder is full in the pipe or between the second electrodes 4, by using the calculated relative dielectric constant.

Next, the connection switching part 35 connects the capacitance measurement and relative dielectric constant calculation unit 30 to the terminal 35b. The capacitance measurement and relative dielectric constant calculation unit 30 receives a signal from the second electrodes 4, measures the second capacitance, and compares the second capacitance with the calculated third capacitance.

The capacitance measurement and relative dielectric constant calculation unit 30 provides the display unit 50 with information regarding the kind of the powder identified as described above, a percentage of the second capacitance relative to the third capacitance, and the second capacitance. Then, the display unit 50 displays the provided information according to any one form of the options 1 to 4. One of the options 1 to 4 may be selected by a user.

Further, the display unit 50 may display the accumulated amount in the unit of percentage, mm (cm), inch or the like.

The described apparatus for measuring the powder thickness according to the preferred embodiments of the present invention may be installed, for example, at any pipes in which the powder is generated at the time of semiconductor production. The apparatus for measuring the powder thickness may be connected to the existing pipe through the bypass pipe (referring to FIG. 3A) or may be inserted in the middle of the existing pipe in series (referring to FIG. 3B).

Further, the powder which can be measured by the apparatus for measuring the powder thickness according to the present invention includes all of dielectric substances and may be, for example, $AlCl_3$, $B_2O$, $B_2O_3$, $BCl_3$, $C_2H_4$, $C_2H_4O$, $C_2H_5$, $CF_4$, $CH_2F_2$, $CH_4$, $CHF_3$, $CO_2$, $CuCl$, $HBr$, $HCl$, $P_2O_3$, $P_2O_5$, $SiF_4$, $SiH_2Cl_2$, $SiN$, $SiO_2$, $TiN$, $WF_6$ or the like.

The apparatus for measuring the thickness of the powder deposited on the inner surface of the pipe according to the embodiments of the present invention as described above can be installed, for example, at a pipe in which the powder flows like a vacuum pipe used at the time of the semiconductor production (of course, it can be used in various pipelines other than the vacuum pipe), and can accurately identify the kind and the thickness of the powder deposited on the inner surface of the pipe. Therefore, since the pipe can be replaced at a suitable time, a safety accident caused by pipe blockage can be prevented, and also unnecessary pipe replacement can be prevented, thereby reducing maintenance costs.

Further, in the above-mentioned embodiment, a pair of first electrodes are provided. However, a plurality of pairs of first electrodes may be provided. In this case, an average of the capacitance measured between each pair of first electrodes may be used. Further, in the above-mentioned embodiment, the first electrodes are made up of a pair of electrodes, but it may be considered that the first electrodes are configured to have three or more electrodes.

Further, in the above-mentioned embodiment, a pair of second electrodes are provided. However, a plurality of pairs of second electrodes may be provided. In this case, an average of capacitances measured between each pair of second electrodes may be used. Further, in the above-mentioned embodiment, the second electrodes are made up of a pair of electrodes, but it may be considered that the second electrodes are configured to have three or more electrodes.

Furthermore, in the above-mentioned embodiment, the pair of first electrodes are disposed at the downstream side of the pair of second electrodes, but may be disposed at an upstream side of the pair of second electrodes.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An apparatus for measuring a thickness of a powder deposited on an inner surface of a pipe, which includes a capacitance measurement part for measuring a capacitance, the apparatus comprising:
a pair of first electrodes spaced from each other, and disposed adjacent to one portion of the inner surface of the pipe; and
a pair of second electrodes spaced from each other symmetrically relative to a center portion of the pipe, and attached to the inner surface of the pipe,
wherein the pair of the first electrodes and the pair of the second electrodes are connected to the capacitance measurement part, wherein a relative dielectric constant of the powder ($\epsilon_r/\epsilon_0$) is calculated using the following Equation:

$$\epsilon_r/\epsilon_0 = C \cdot d/A \qquad \text{Equation}$$

where $\epsilon_r$ is a dielectric constant of the powder, $\epsilon_0$ is a dielectric constant of vacuum, C is a first capacitance corresponding to a capacitance measured between the pair of the first electrodes when it is not changed, d is a gap between the pair of the first electrodes, and A is a surface area of the first electrode,
and wherein a kind of the powder may be identified by the calculated relative dielectric constant of the powder.

2. The apparatus of claim 1, wherein the pair of the first electrodes are disposed at a downstream side of the pair of the second electrodes in a flow direction of a fluid passing through the pipe.

3. The apparatus of claim 1, further comprising a protrusion member provided on the inner surface of the pipe, wherein the protrusion member is disposed at a downstream side of the pair of the first electrodes in a flow direction of a fluid passing through the pipe, so as to be adjacent to the pair of the first electrodes.

4. The apparatus of claim 3, wherein a height of one of the pair of the first electrodes, which is further adjacent to the center portion of the pipe, is substantially equal to a height of the protrusion member.

5. The apparatus of claim 1, wherein the gap between the pair of the first electrodes is more than 0 mm, but less than 10 mm.

6. The apparatus of claim 1, wherein a third capacitance of the pair of the second electrodes corresponding to a state at which the identified powder is full between the pair of the second electrodes is compared with a second capacitance which is currently measured between the pair of the second electrodes,
wherein the third capacitance is calculated using the following Equation:

$$\epsilon_r/\epsilon_0 = C \cdot d/A \qquad \text{Equation}$$

where $\epsilon_r/\epsilon_0$ is the relative dielectric constant of the powder, C is the third capacitance, d is a gap between the pair of the second electrodes, and A is a surface area of the second electrode.

7. An apparatus for measuring a thickness of a powder deposited on an inner surface of a pipe, comprising:
a housing for being connected to the pipe;
a pair of first electrodes spaced from each other, and disposed adjacent to one portion of an inner surface of the housing;

a pair of second electrodes spaced from each other symmetrically relative to a center portion of the housing, and attached to the inner surface of the housing; and a capacitance measurement and relative dielectric constant calculation unit connected to the pair of the first electrodes and the pair of the second electrodes, wherein the capacitance measurement and relative dielectric constant calculation unit calculates a relative dielectric constant of the powder ($\epsilon_r/\epsilon_0$) by inputting a first capacitance corresponding to a capacitance measured between the pair of the first electrodes when it is not changed, into the following Equation:

$$\epsilon_r/\epsilon_0 = C \cdot d/A \qquad \text{Equation}$$

where $\epsilon_r$ is a dielectric constant of the powder, $\epsilon_0$ is a dielectric constant of vacuum, C is the first capacitance, d is a gap between the pair of the first electrodes, and A is a surface area of the first electrode.

8. The apparatus of claim 7, further comprising a connection switching part, wherein the connection switching part selectively connects the capacitance measurement and relative dielectric constant calculation unit to the pair of the first electrodes or the pair of the second electrodes.

9. The apparatus of claim 7, wherein the capacitance measurement and relative dielectric constant calculation unit calculates a thickness of the powder deposited on the inner surface of the pipe by comparing a third capacitance of the pair of the second electrodes corresponding to a state at which the identified powder is full between the pair of the second electrodes with a second capacitance which is currently measured between the pair of the second electrodes, wherein the third capacitance is calculated using the following Equation:

$$\epsilon E_r/\epsilon_0 = C \cdot d/A \qquad \text{Equation}$$

where $\epsilon_r/\epsilon_0$ is the relative dielectric constant of the powder, C is the third capacitance, d is a gap between the pair of the second electrodes, and A is a surface area of the second electrode.

10. The apparatus of claim 9, further comprising a display unit, wherein the display unit receives a signal from the capacitance measurement and relative dielectric constant calculation unit and displays an accumulated amount of the powder deposited on the inner surface of the pipe.

11. The apparatus of claim 9, further comprising a display unit, wherein the display unit receives a signal from the capacitance measurement and relative dielectric constant calculation unit and displays a kind of the powder deposited on the inner surface of the pipe.

12. The apparatus of claim 7, wherein at least one pair of the pair of the first electrodes and the pair of the second electrodes are connected to the capacitance measurement and relative dielectric constant calculation unit through a LAN cable or Wi-Fi.

13. The apparatus of claim 7, wherein the pair of the first electrodes are located at a downstream side of the pair of the second electrodes in a flow direction of a fluid passing through the housing.

14. The apparatus of claim 7, further comprising a protrusion member provided on the inner surface of the housing, wherein the protrusion member is disposed at a downstream side of the pair of the first electrodes in a flow direction of a fluid passing through the housing, so as to be adjacent to the pair of the first electrodes.

15. The apparatus of claim 14, wherein a height of one of the pair of the first electrodes, which is further adjacent to the center portion of the housing, is substantially equal to a height of the protrusion member.

16. The apparatus of claim 1, wherein the pair of the first electrodes are used to measure static electricity.

17. The apparatus of claim 7, wherein the pair of the first electrodes are used to measure static electricity.

18. A method of measuring a thickness of a powder deposited on an inner surface of a pipe, comprising:

measuring a first capacitance at a pair of first electrodes spaced from each other, and disposed adjacent to one portion of the inner surface of the pipe, the first capacitance corresponding to a capacitance measured between the pair of the first electrodes when it is not changed;

identifying a kind of powder deposited on the inner surface of the pipe from a relative dielectric constant ($\epsilon_r/\epsilon_0$) calculated by inputting the first capacitance into the following Equation (1);

$$\epsilon_r/\epsilon_0 = C \cdot d/A \qquad \text{Equation (1)}$$

where $\epsilon_r$ is a dielectric constant of the powder, $\epsilon_0$ is a dielectric constant of vacuum, C is the first capacitance, d is a gap between the pair of the first electrodes, and A is a surface area of the first electrode, measuring a second capacitance at a pair of second electrodes spaced from each other symmetrically relative to a center portion of the pipe, and attached to the inner surface of the pipe;

calculating a third capacitance of the pair of the second electrodes corresponding to a state at which the identified powder is full between the pair of the second electrodes, the third capacitance being calculated using the following Equation (2):

$$\epsilon_r/\epsilon_0 = C \cdot d/A \qquad \text{Equation (2)}$$

where $\epsilon_r/\epsilon_0$ is the relative dielectric constant of the powder, C is the third capacitance, d is a gap between the pair of the second electrodes, and A is a surface area of the second electrode; and comparing the second capacitance with the third capacitance.

* * * * *